US012721565B2

(12) United States Patent
Katz et al.

(10) Patent No.: US 12,721,565 B2
(45) Date of Patent: Sep. 1, 2026

(54) AUTOMATED TOOL FOR VEIN SHAVING IN ANATOMICAL MAP

(71) Applicant: Biosense Webster (Israel) Ltd., Yokneam (IL)

(72) Inventors: Natan Sharon Katz, Atlit (IL); Fady Massarwa, Baka al Gharbiyya (IL); Vincent Alexandre Roger, Caluire-et-cuire (FR)

(73) Assignee: Biosense Webster (Israel) Ltd., Yokneam (IL)

( * ) Notice: Subject to any disclaimer, the term of this patent is extended or adjusted under 35 U.S.C. 154(b) by 294 days.

(21) Appl. No.: 18/438,066

(22) Filed: Feb. 9, 2024

(65) Prior Publication Data

US 2025/0255535 A1 Aug. 14, 2025

(51) Int. Cl.

*A61B 5/367* (2021.01)
*A61B 5/00* (2006.01)
*A61B 5/287* (2021.01)

(52) U.S. Cl.

CPC .............. *A61B 5/367* (2021.01); *A61B 5/287* (2021.01); *A61B 5/7203* (2013.01); *A61B 5/742* (2013.01)

(58) Field of Classification Search

CPC ....... A61B 5/367; A61B 5/287; A61B 5/7203; A61B 5/742; A61B 2576/023; A61B 5/0044; G16H 30/40; G06T 7/0012

See application file for complete search history.

(56) References Cited

U.S. PATENT DOCUMENTS

| | | | | |
|---|---|---|---|---|
| 6,106,466 | A | 8/2000 | Sheehan et al. | |
| 10,561,325 | B2 | 2/2020 | Markovitz | |
| 11,532,082 | B2 | 12/2022 | Cohen et al. | |
| 2005/0018890 | A1 | 1/2005 | McDonald et al. | |
| 2014/0278232 | A1* | 9/2014 | Miller | G16H 50/50 702/168 |
| 2016/0183824 | A1* | 6/2016 | Severino | A61B 5/339 600/523 |

(Continued)

FOREIGN PATENT DOCUMENTS

| | | | | |
|---|---|---|---|---|
| EP | 1912174 A2 * | 4/2008 | | A61B 5/103 |
| EP | 2824639 A2 | 1/2015 | | |
| WO | 2023126720 A1 | 7/2023 | | |

OTHER PUBLICATIONS

Extended European Search Report issued on Jun. 18, 2025 for European Patent Application No. 25156419.1.

(Continued)

*Primary Examiner* — Michael J Lau
(74) *Attorney, Agent, or Firm* — Volpe Koenig

(57) ABSTRACT

An automated technique for revising an electro-anatomical map generated using a catheter having a plurality of electrodes. A first electro-anatomical map that includes an anatomical structure having a mapped volume with a substantially tubular shape is displayed, and one or more points along medial axis of the mapped volume are estimated. At a first cross-section of the mapped volume, a first best-fitting ellipse is determined. A generalized cylindrical volume is calculated between the first cross-section and a second cross-section in accordance with at least the first best-fitting ellipse. Data points from the mapped volume that are outside of the generalized cylindrical volume are removed and a revised map is displayed.

20 Claims, 12 Drawing Sheets

(56) References Cited

U.S. PATENT DOCUMENTS

| | | | | |
|---|---|---|---|---|
| 2018/0177552 | A1* | 6/2018 | Zoabi | A61B 5/283 |
| 2019/0183367 | A1* | 6/2019 | Turgeman | A61B 5/367 |
| 2023/0068315 | A1* | 3/2023 | Safran | G06T 17/00 |
| 2023/0157569 | A1* | 5/2023 | Govari | G16H 20/40<br>600/374 |
| 2023/0210437 | A1* | 7/2023 | Beeckler | A61B 5/367<br>600/523 |

OTHER PUBLICATIONS

Meuschke, G., et al., “Vessel Maps: A Survey of Map-Like Visualizations of the Cardiovascular System”, Article, Chapter 1: Monte Carlo Path Tracing, Wiley-Blackwell, Oxford, (2022).

* cited by examiner

AUTOMATED TOOL FOR VEIN SHAVING IN ANATOMICAL MAP

FIELD OF INVENTION

The present invention is related to anatomical mapping. More particularly, the present invention relates to improving the visualization of anatomical structures such as veins in an electro-anatomical map.

BACKGROUND

Some clinical procedures employ techniques for the analysis of a computerized anatomical map of an organ. For example, in electrophysiology (EP) procedures such as catheter-based radio frequency (RF) ablation for pulmonary vein isolation (a first line of treatment for atrial fibrillation (AF)), an anatomical map of a heart chamber is generated and used. Fast anatomical mapping (FAM) is one algorithm for building such an anatomical map from electrical signals captured by a catheter on a myocardium. The anatomical map is used to guide a physician to desired ablation sites. As part of the building of the anatomical map (e.g., an aspect of generating the anatomical map of the FAM), a technician can modify the volume of the FAM by performing a manual, time consuming process of shaving. Shaving occurs for a variety of reasons, including, e.g., to present a more anatomically accurate representation and/or to resolve visual artifacts in the map.

With existing mapping techniques, artifacts of the mapping process can cause anatomical structures such as veins to appear narrow in one portion of the vein and larger in a neighboring portion of the vein. Such a visualization can imply that a pulmonary vein stenosis is present at the site where the vein is narrow. In order to remove such artifacts, manual shaving of the map is typically performed by an operator. When addressing an artifact such as that described above (implying a pulmonary vein stenosis), voxels are manually removed (shaved) from the volume of the vein until the vein has a more constant volume. An automated solution to this manual shaving process is needed.

SUMMARY

An automated technique for revising an electro-anatomical map (e.g., a FAM) is provided. The map is generated using a catheter having a plurality of electrodes. As the catheter moves within the body during a medical procedure, the map is generated based on data points acquired using the electrodes, and is subsequently revised. Initially, a first electro-anatomical map that includes an anatomical structure having a mapped volume with a substantially tubular shape is displayed on a user interface. At a first cross-section of the mapped volume, a first best-fitting ellipse is determined based on data points associated with the first cross-section of the mapped volume. A first point along a medial axis of the mapped volume is estimated in accordance with a center of the first best-fitting ellipse. A second point along the medial axis on a second cross-section of the mapped volume is estimated; the first-cross section being different from the second cross-section. A generalized cylindrical volume spanning between the first cross-section and the second cross-section is calculated in accordance with at least the first best-fitting ellipse. Data points from the mapped volume that are outside of the generalized cylindrical volume are removed. A second electro-anatomical map having an updated version of the anatomical structure generated without the removed data points is displayed on the user interface.

In some examples, a plurality of points defining the medial axis are determined. In some of these examples, the first cross-section is normal to the medial axis and the second point is estimated by selecting one of the plurality of points defining the medial axis.

In some examples, further points along the medial axis on further cross-sections of the mapped volume are estimated and the generalized cylindrical volume spans the first cross-section, the second cross-section and the further cross-sections.

In some examples, the anatomical structure is a vein associated with a heart muscle, data points associated with the first cross-section of the mapped volume correspond to ablation tags, and data points associated with the second cross-section and each of the further cross-sections of the mapped volume do not correspond to ablation tags.

In some examples, more than two best-fitting ellipses are determined based on data points associated with other cross-sections of the mapped volume, and the generalized cylindrical volume is calculated accordance with more than two-best fitting ellipses.

In some examples, the first best-fitting ellipse is a circle, and the substantially tubular shape is a ruled surface or generalized cylinder. In other embodiments, a best-fitting spline is used.

According to one or more embodiments, the exemplary embodiments above can be implemented as methods, apparatuses, systems, and/or computer program products.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION

Disclosed herein is a method and/or system for anatomical mapping. The method and/or system includes a processor executable code or software that is necessarily rooted in process operations by, and in processing hardware of, medical device equipment performing and using the anatomical mapping. For ease of explanation, the anatomical map is described herein with respect to mapping a heart. However, any anatomical structure, body part, organ, or portion thereof can be a target for mapping using the techniques described herein.

According to one or more embodiments, the methods and systems disclosed herein generate anatomical maps of the heart that include an endocardial surface of a left atrium (LA). A map can be one three-dimensional (3D) model or a combination of multiple 3D models. The methods and systems can generate and edit the maps of the heart and provide real-time or post-processed maps during or in connection with an EP procedure (e.g., an ablation procedure). By way of example, the methods and systems can revise an anatomical map using the techniques disclosed herein, thereby improving the operations and outcomes of the anatomical mapping.

Figure 1:
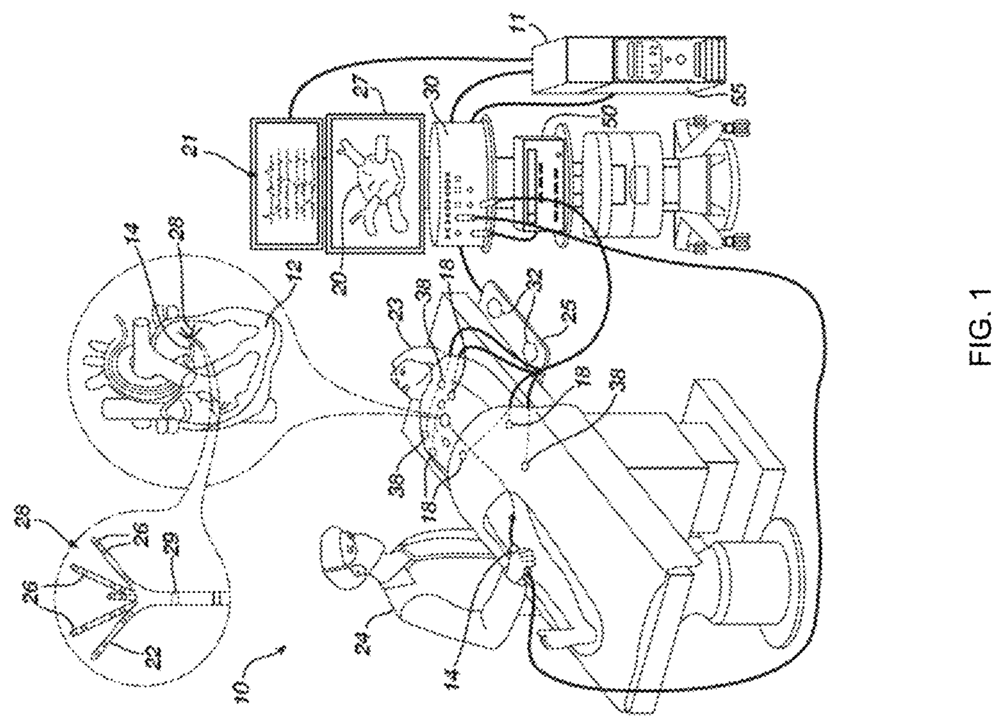
FIG. 1 depicts an example catheter-based electrophysiology mapping and ablation system according to one or more embodiments.

Reference is made to FIG. 1 showing an example system (e.g., medical device equipment and/or catheter-based electrophysiology mapping and ablation system), shown as system 10, in which one or more features of the subject matter herein can be implemented according to one or more embodiments. All or part of the system 100 can be used to collect information (e.g., biometric data) and/or used to implement the map revision techniques as described herein. In some examples, such techniques are implemented using a processor executable code or software that is stored on a memory of the system 10 and that is necessarily rooted in process operations by, and in processing hardware of, the system 10.

FIG. 1 illustrates a recorder 11, a heart 12, a catheter 14, a model or anatomical map 20, an electrogram 21, a spline 22, a patient 23, a physician 24 (which is representative of any medical professional, technician, clinician, operator, clinical support specialist, clinical account specialist, healthcare personnel, etc.), a location pad 25, one or more electrodes 26, a display device 27, a distal tip 28, a sensor 29, a coil 32, a patient interface unit (PIU) 30, electrode skin patches 38, an ablation energy generator 50, and a workstation 55. Note further each element and/or item of the system 10 is representative of one or more of that element and/or that item. The example system 10 shown in FIG. 1 implements the embodiments disclosed herein. The disclosed embodiments can similarly be applied using other system components and settings. Additionally, the system 10 can include additional components, for example elements for sensing electrical activity, wired or wireless connectors, processing and display devices, or other components.

The system 10 includes multiple catheters 14, which are percutaneously inserted by the physician 24 through the patient's vascular system into a chamber or vascular structure of the heart 12. Typically, a delivery sheath catheter is inserted into the left or right atrium near a desired location in the heart 12. Thereafter, a plurality of catheters can be inserted into the delivery sheath catheter to arrive at the desired location. The plurality of catheters 14 may include catheters dedicated for sensing Intracardiac Electrogram (IEGM) signals, catheters dedicated for ablating, and/or catheters dedicated for both sensing and ablating. The example catheter 14 that is configured for sensing IEGM is illustrated herein. The physician 24 brings the distal tip 28 of the catheter 14 into contact with a heart wall for sensing a target site in the heart 12. For ablation, the physician 24 would similarly bring a distal end of an ablation catheter to a target site for ablating.

The catheter 14 is an exemplary catheter that includes at least one and preferably multiple electrodes 26 optionally distributed over a plurality of splines 22 at the distal tip 28 and configured to sense the IEGM signals. The catheter 14 may additionally include the sensor 29 embedded in or near the distal tip 28 for tracking position and orientation of the distal tip 28. Optionally and preferably, the position sensor 29 is a magnetic based position sensor including three magnetic coils for sensing 3D position and orientation. According to one or more embodiments, shape and parameters of the catheter 14 vary based on whether the catheter 14 is used for diagnostic or ablation purposes, the type of arrhythmia, patient anatomy, and other factors, which affects catheter maneuverability (e.g., an ability to touch without bending the surface and the tracked parts of the catheter 14). The shape and parameters of the catheter 14 also impact the accuracy of anatomical maps. Large spherical single-shot catheters, which can ablate a pulmonary vein within seconds, have become popular but require guidance from fluoroscopy, CT/MRI, or additional mapping catheters.

The sensor 29 (e.g., a position or a magnetic based position sensor) may be operated together with the location pad 25 including a plurality of magnetic coils 32 configured to generate magnetic fields in a predefined working volume. Real time position of the distal tip 28 of the catheter 14 may be tracked based on magnetic fields generated with the location pad 25 and sensed by the sensor 29. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

The system 10 includes one or more electrode patches 38 positioned for skin contact on the patient 23 to establish location reference for the location pad 25 as well as impedance-based tracking of the electrodes 26. For impedance-based tracking, electrical current is directed toward the electrodes 26 and sensed at the patches 38 (e.g., electrode skin patches) so that the location of each electrode can be triangulated via the patches 38. Details of the impedance-based location tracking technology are described in U.S. Pat. Nos. 7,536,218; 7,756,576; 7,848,787; 7,869,865; and 8,456,182, which are incorporated herein by reference.

The recorder 11 displays the electrograms 21 captured with the electrodes 18 (e.g., body surface electrocardiogram (ECG) electrodes) and intracardiac electrograms (IEGM) captured with the electrodes 26 of the catheter 14. The recorder 11 may include pacing capability for pacing the heart rhythm and/or may be electrically connected to a standalone pacer.

The system 10 may include the ablation energy generator 50 that is adapted to conduct ablative energy to the one or more of electrodes 26 at the distal tip 28 of the catheter 14 configured for ablating. Energy produced by the ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

The PIU 30 is an interface configured to establish electrical communication between catheters, electrophysiological equipment, power supply and the workstation 55 for controlling operation of the system 10. Electrophysiological equipment of the system 10 may include for example, multiple catheters 14, the location pad 25, the body surface ECG electrodes 18, the electrode patches 38, the ablation energy generator 50, and the recorder 11. Optionally and preferably, the PIU 30 additionally includes processing capability for implementing real-time computations of location of the catheters and for performing ECG calculations.

The workstation 55 includes memory, a processor unit with memory or storage with appropriate operating software loaded therein, and user interface capability. The workstation 55 may provide multiple functions, optionally including modeling the endocardial anatomy in three-dimensions (3D) and rendering the model or anatomical map 20 (e.g., a visualization) for display on the display device 27, displaying on the display device 27 activation sequences (or other data) compiled from recorded electrograms 21 in representative visual indicia or imagery superimposed on the rendered anatomical map 20, displaying real-time location and orientation of multiple catheters within the heart chamber, and displaying on the display device 27 sites of interest for example places where ablation energy has been applied. One commercial product embodying elements of the system 10 is available as the CARTO™ 3 System, available from Biosense Webster, Inc., 31A Technology Drive, Irvine, CA 92618. Note that modeling the endocardial anatomy in 3D can include generating a surface thereof as a triangular mesh.

For instance, the system 10 can be part of a surgical system (e.g., CARTO® system sold by Biosense Webster) that is configured to obtain biometric data (e.g., anatomical and electrical measurements of a patient's organ, for example the heart 12 and as described herein) and perform a cardiac ablation procedure. More particularly, treatments for cardiac conditions for example cardiac arrhythmia often require obtaining a detailed mapping of cardiac tissue, chambers, veins, arteries and/or electrical pathways. For example, a prerequisite for performing a catheter ablation successfully is that the cause of the cardiac arrhythmia is accurately located in a chamber of the heart 12. Such locating may be done via an electrophysiological investigation during which electrical potentials are detected and spatially resolved with a mapping catheter (e.g., the catheter 14) introduced into the chamber of the heart 12. This electrophysiological investigation, the so-called electro-anatomical mapping, thus provides 3D mapping data which can be displayed on the display device 27. In many cases, the mapping function and a treatment function (e.g., ablation) are provided by a single catheter or group of catheters such that the mapping catheter also operates as a treatment catheter at the same time.

Figure 2:
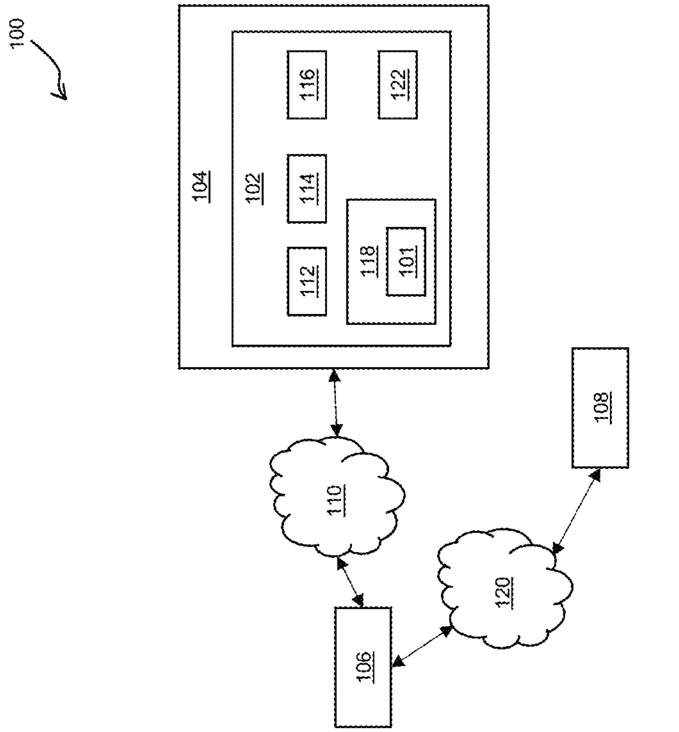
FIG. 2 is a block diagram of an example system for remotely monitoring and communicating biometric data according to one or more embodiments.

FIG. 2 is a block diagram of an example system 100 for remotely monitoring and communicating biometric data (e.g., patient biometrics). In the example illustrated in FIG. 2, the system 100 includes a patient biometric monitoring and processing apparatus 102 associated with a patient 104, a local computing device 106, a remote computing system 108, a first network 110, a patient biometric sensor 112, a processor 114, a user input (UI) sensor 116, a memory 118, a second network 120, and a transmitter-receiver (i.e., transceiver) 122.

According to one or more embodiments, the patient biometric monitoring and processing apparatus 102 may be an apparatus that is internal to the patient's body (e.g., subcutaneously implantable), for example the catheter 14 of FIG. 1. The patient biometric monitoring and processing apparatus 102 may be inserted into a patient via any applicable manner including orally injecting, surgical insertion via a vein or artery, an endoscopic procedure, or a laparoscopic procedure.

According to one or more embodiments, the patient biometric monitoring and processing apparatus 102 may be an apparatus that is external to the patient, for example the electrode patches 38 of FIG. 1. For example, as described in more detail below, the patient biometric monitoring and processing apparatus 102 may include an attachable patch (e.g., that attaches to a patient's skin). The monitoring and processing apparatus 102 may also include a catheter with one or more electrodes, a probe, a blood pressure cuff, a weight scale, a bracelet or smart watch biometric tracker, a glucose monitor, a continuous positive airway pressure (CPAP) machine or virtually any device which may provide an input concerning the health or biometrics of the patient.

According to one or more embodiments, the patient biometric monitoring and processing apparatus 102 may include both components that are internal to the patient and components that are external to the patient.

A single patient biometric monitoring and processing apparatus 102 is shown in FIG. 2. Example systems may, however, include a plurality of patient biometric monitoring and processing apparatuses. A patient biometric monitoring and processing apparatus may be in communication with one or more other patient biometric monitoring and processing apparatuses. Additionally or alternatively, a patient biometric monitoring and processing apparatus may be in communication with the network 110.

One or more patient biometric monitoring and processing apparatuses 102 may acquire biometric data (e.g., patient biometrics, for example electrical signals, blood pressure, temperature, blood glucose level, or other biometric data) and receive at least a portion of the biometric data representing the acquired patient biometrics and additional information associated with the acquired patient biometrics from one or more other patient biometric monitoring and processing apparatuses 102. The additional information may be, for example, diagnosis information and/or additional information obtained from an additional device, for example a wearable device. Each of the patient biometric monitoring and processing apparatus 102 may process data, including its own biometric data as well as data received from one or more other patient biometric monitoring and processing apparatuses 102.

Biometric data (e.g., patient biometrics, patient data, or patient biometric data) can include one or more of local activation times (LATs), electrical activity, topology, bipolar mapping, reference activity, ventricle activity, dominant frequency, impedance, or other data. The LAT can be a point in time of a threshold activity corresponding to a local activation, calculated based on a normalized initial starting point. Electrical activity can be any applicable electrical signals that can be measured based on one or more thresholds and can be sensed and/or augmented based on signal to noise ratios and/or other filters. A topology can correspond to the physical structure of a body part or a portion of a body part and can correspond to changes in the physical structure relative to different parts of the body part or relative to different body parts. A dominant frequency can be a frequency or a range of frequency that is prevalent at a portion of a body part and can be different in different portions of the same body part. For example, the dominant frequency of a PV of a heart can be different than the dominant frequency of the right atrium of the same heart. Impedance can be the resistance measurement at a given area of a body part.

Examples of biometric data include, but are not limited to, patient identification data, intracardiac electrocardiogram (IC ECG) data, bipolar intracardiac reference signals, anatomical and electrical measurements, trajectory information, body surface (BS) ECG data, historical data, brain biometrics, blood pressure data, ultrasound signals, radio signals, audio signals, two- or three-dimensional image data, blood glucose data, and temperature data. The biometrics data can be used, generally, to monitor, diagnosis, and treat any number of various diseases, for example cardiovascular diseases (e.g., arrhythmias, cardiomyopathy, and coronary artery disease) and autoimmune diseases (e.g., type I and type II diabetes). Note that BS ECG data can include data and signals collected from electrodes on a surface of a patient, IC ECG data can include data and signals collected from electrodes within the patient, and ablation data can include data and signals collected from tissue that has been ablated. Further, BS ECG data, IC ECG data, and ablation data, along with catheter electrode position data, can be derived from one or more procedure recordings.

In FIG. 2, the network 110 is an example of a short-range network (e.g., local area network (LAN), or personal area network (PAN)). Information may be sent, via the network 110, between the patient biometric monitoring and processing apparatus 102 and the local computing device 106 using any one of various short-range wireless communication protocols, for example Bluetooth, Wi-Fi, Zigbee, Z-Wave, near field communications (NFC), ultraband, or infrared (IR).

The network 120 may be a wired network, a wireless network or include one or more wired and wireless networks. For example, the network 120 may be a long-range network (e.g., wide area network (WAN), the internet, or a cellular network). Information may be sent, via the network 120 using any one of various long-range wireless communication protocols (e.g., TCP/IP, HTTP, 3G, 4G/LTE, or 5G/New Radio).

The patient biometric monitoring and processing apparatus 102 may include the patient biometric sensor 112, the processor 114, the UI sensor 116, the memory 118, and the transceiver 122. The patient biometric monitoring and processing apparatus 102 may continually or periodically monitor, store, process and communicate, via the network 110, any number of various biometric data. Examples of biometric data include electrical signals (e.g., ECG signals and brain biometrics), blood pressure data, blood glucose data, and temperature data. The biometric data may be monitored and communicated for treatment across any number of various diseases, for example cardiovascular diseases (e.g., arrhythmias, cardiomyopathy, and coronary artery disease) and autoimmune diseases (e.g., type I and type II diabetes).

The patient biometric sensor 112 may include, for example, one or more sensors configured to sense a type of biometric data. For example, the patient biometric sensor 112 may include an electrode configured to acquire electrical signals (e.g., heart signals, brain signals or other bioelectrical signals), a temperature sensor, a blood pressure sensor, a blood glucose sensor, a blood oxygen sensor, a pH sensor, an accelerometer and a microphone.

As described in more detail below, the patient biometric monitoring and processing apparatus 102 may be an ECG monitor for monitoring ECG signals of a heart (e.g., the heart 12). The patient biometric sensor 112 of the ECG monitor may include one or more electrodes for acquiring ECG signals. The ECG signals may be used for treatment of various cardiovascular diseases, as well as anatomical mapping.

The transceiver 122 may include a separate transmitter and receiver. Alternatively, the transceiver 122 may include a transmitter and receiver integrated into a single device.

The processor 114 may be configured to store biometric data in the memory 118 acquired by the patient biometric sensor 112 and to communicate the biometric data across the network 110 via a transmitter of the transceiver 122. Data from one or more other patient biometric monitoring and processing apparatus 102 may also be received by a receiver of the transceiver 122, as described in more detail herein. By way of example, the automated map revision techniques described herein are implemented as a processor executable code or software that can be stored on the memory 118 (as shown) and executed by the processor 114. By way of further example, the automated map revision techniques are implemented as code stored and executed on the local computing device 106 and/or the remote computing system 108. Thus, the operation of the automated map revision techniques is necessarily rooted in process operations by, and in processing hardware of, the system 100.

According to one or more embodiments, system 100 operates to generate on a display (e.g., display device 27) an initial visualization (e.g., a first electro-anatomical map) during an ablation procedure. The initial visualization is generated from data points sensed by a catheter positioned in a patent, and includes an anatomical structure (e.g., a vein) having a mapped volume with a substantially tubular shape. Applying the techniques described in connection with FIGS. 5-12 below, system 100 determines, at a first cross-section of the mapped volume, a first best-fitting ellipse based on data points associated with the first cross-section. A first point along a medial axis of the mapped volume is estimated in accordance with (e.g., from) a center of the first best-fitting ellipse. A second point along the medial axis on a second cross-section of the mapped volume is estimated; the first-cross section being different from the second cross-section. A generalized cylindrical volume that spans between the first cross-section and the second cross-section is calculated in accordance with at least the first best-fitting ellipse. System 100 removes data points from the mapped volume that are outside of the generalized cylindrical volume. A second electro-anatomical map having an updated version of the anatomical structure generated without the removed data points is displayed (e.g., on display device 27) as part of a user interface.

In some examples, the anatomical structure is a vein associated with a heart muscle, data points associated with the first cross-section of the mapped volume correspond to ablation tags, and data points associated with the second cross-section and additional cross-sections of the mapped volume do not correspond to ablation tags.

In some examples, a plurality of points defining the medial axis are determined. In some of these examples, the first cross-section is normal to the medial axis and the second point is estimated by selecting one of the plurality of points defining the medial axis.

According to one or more embodiments, the patient biometric monitoring and processing apparatus 102 includes UI sensor 116 that may be, for example, a piezoelectric sensor or a capacitive sensor configured to receive a user input, for example a tapping or touching. For example, the UI sensor 116 may be controlled to implement a capacitive coupling, in response to tapping or touching a surface of the patient biometric monitoring and processing apparatus 102 by the patient 104. Gesture recognition may be implemented via any one of various capacitive types, for example resistive capacitive, surface capacitive, projected capacitive, surface acoustic wave, piezoelectric and infrared touching. Capacitive sensors may be disposed at a small area or over a length of the surface such that the tapping or touching of the surface activates the monitoring device.

As described in more detail below, the processor 114 may be configured to respond selectively to different tapping patterns of the capacitive sensor (e.g., a single tap or a double tap), which may be the UI sensor 116, such that different tasks of the patch (e.g., acquisition, storing, or transmission of data) may be activated based on the detected pattern. In some embodiments, audible feedback may be given to the user from the patient biometric monitoring and processing apparatus 102 when a gesture is detected.

The local computing device 106 of the system 100 is in communication with the patient biometric monitoring and processing apparatus 102 and may be configured to act as a gateway to the remote computing system 108 through the second network 120. The local computing device 106 may be, for example, a, smart phone, smartwatch, tablet or other portable smart device configured to communicate with other devices via the network 120. Alternatively, the local computing device 106 may be a stationary or standalone device, for example a stationary base station including, for example, modem and/or router capability, a desktop or laptop computer using an executable program to communicate information between the patient biometric monitoring and processing apparatus 102 and the remote computing system 108 via the PC's radio module, or a USB dongle. Biometric data may be communicated between the local computing device 106 and the patient biometric monitoring and processing apparatus 102 using a short-range wireless technology standard (e.g., Bluetooth, Wi-Fi, ZigBee, Z-wave and other short-range wireless standards) via the short-range wireless network 110, for example a local area network (LAN) (e.g., a personal area network (PAN)). In some embodiments, the local computing device 106 may also be configured to display the acquired patient electrical signals and information associated with the acquired patient electrical signals, as described in more detail herein.

In some embodiments, the remote computing system 108 may be configured to receive at least one of the monitored patient biometrics and information associated with the monitored patient via network 120, which is a long-range network. For example, if the local computing device 106 is a mobile phone, network 120 may be a wireless cellular network, and information may be communicated between the local computing device 106 and the remote computing system 108 via a wireless technology standard, for example any of the wireless technologies mentioned above. As described in more detail below, the remote computing system 108 may be configured to provide (e.g., visually display and/or aurally provide) the at least one of the patient biometrics and the associated information to the physician 24.

Figure 3:
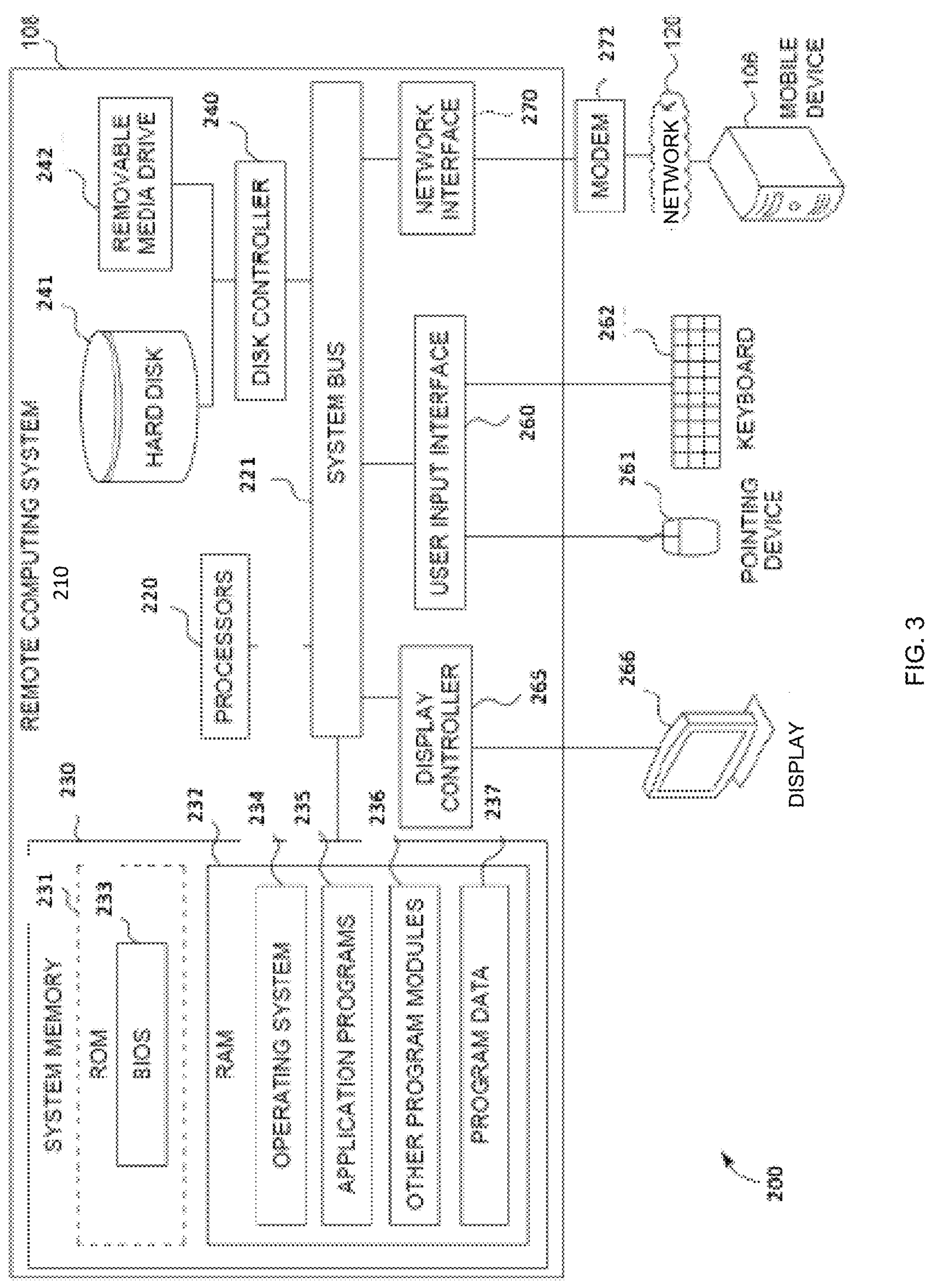
FIG. 3 is a system diagram of an example computing environment in communication with a network according to one or more embodiments.

FIG. 3 is a system diagram of an example of a computing environment 200 in communication with network 120. In some instances, the computing environment 200 is incorporated in a public cloud computing platform (e.g., Amazon Web Services or Microsoft Azure), a hybrid cloud computing platform (e.g., HP Enterprise OneSphere) or a private cloud computing platform.

As shown in FIG. 3, computing environment 200 includes a computer system 210, which is one example of the workstation 55 of FIG. 1, the local computing device 106 of FIG. 2, and/or the remote computing system 108 of FIG. 2 upon which embodiments described herein may be implemented. By way of example, the tenting detection and correction techniques described herein are implemented as a processor executable code or software that can be stored on the system memory 231 (as shown) and executed by processors 220, and rooted in process operations by, and in processing hardware of, the computing environment 200.

The computer system 210 may, via processors 220, which may include one or more processors, perform various functions. The functions may include analyzing monitored biometric data and the associated information and, according to physician-determined or algorithm driven thresholds and parameters, providing (e.g., via display 266) alerts, additional information or instructions. The functions may include the operation of the tenting error and correction techniques as described herein. As described in more detail herein, the computer system 210 may be used to provide (e.g., via display 266) the physician 24 of FIG. 1 with a dashboard of patient information, such that such information may enable the physician 24 to identify and prioritize patients having more critical needs than others.

As shown in FIG. 3, the computer system 210 may include a communication mechanism, for example a bus 221 or other communication mechanism for communicating information within the computer system 210. The computer system 210 further includes one or more processors 220 coupled with the bus 221 for processing the information. The processors 220 may include one or more CPUs, GPUs, or any other processor known in the art.

The computer system 210 also includes a system memory 230 coupled to the bus 221 for storing information and instructions to be executed by processors 220. The system memory 230 may include computer readable storage media in the form of volatile and/or nonvolatile memory, for example read only system memory (ROM) 231 and/or random-access memory (RAM) 232. The system memory RAM 232 may include other dynamic storage device(s) (e.g., dynamic RAM, static RAM, and synchronous DRAM). The system memory ROM 231 may include other static storage device(s) (e.g., programmable ROM, erasable PROM, and electrically erasable PROM). In addition, the system memory 230 may be used for storing temporary variables or other intermediate information during the execution of instructions by the processors 220. A basic input/output system 233 (BIOS) may contain routines to transfer information between elements within computer system 210, for example during start-up, that may be stored in system memory ROM 231. RAM 232 may comprise data and/or program modules that are immediately accessible to and/or presently being operated on by the processors 220. System memory 230 may additionally include, for example, operating system 234, application programs 235, other program modules 236 and program data 237.

The illustrated computer system 210 also includes a disk controller 240 coupled to the bus 221 to control one or more storage devices for storing information and instructions, for example a magnetic hard disk 241 and a removable media drive 242 (e.g., floppy disk drive, compact disc drive, tape drive, and/or solid-state drive). The storage devices may be added to the computer system 210 using an appropriate device interface (e.g., a small computer system interface (SCSI), integrated device electronics (IDE), Universal Serial Bus (USB), or FireWire).

The computer system 210 may also include a display controller 265 coupled to the bus 221 to control a monitor or display 266, for example a cathode ray tube (CRT) or liquid crystal display (LCD), for displaying information to a computer user. The illustrated computer system 210 includes a user input interface 260 and one or more input devices, for example a keyboard 262 and a pointing device 261, for interacting with a computer user and providing information to the processor 220. The pointing device 261, for example, may be a mouse, a trackball, or a pointing stick for communicating direction information and command selections to the processor 220 and for controlling cursor movement on the display 266. The display 266 may provide a touch screen interface that may allow input to supplement or replace the communication of direction information and command selections by the pointing device 261 and/or keyboard 262.

The computer system 210 may perform a portion or each of the functions and methods described herein in response to the processors 220 executing one or more sequences of one or more instructions contained in a memory, for example, the system memory 230. Such instructions may be read into the system memory 230 from another computer readable medium, for example, a hard disk 241 or a removable media drive 242. The hard disk 241 may contain one or more data stores and data files used by embodiments described herein. Data store contents and data files may be encrypted to improve security. The processors 220 may also be employed in a multi-processing arrangement to execute the one or more sequences of instructions contained in system memory 230. In alternative embodiments, hard-wired circuitry may be used in place of or in combination with software instructions. Thus, embodiments are not limited to any specific combination of hardware circuitry and software.

As stated above, the computer system 210 may include at least one computer readable medium or memory for holding instructions programmed according to embodiments described herein (e.g., embodiments of the tenting error detection and correction techniques) and for containing data structures, tables, records, or other data described herein. The term computer readable medium as used herein refers to any non-transitory, tangible medium that participates in providing instructions to the processor 220 for execution. A computer readable medium may take many forms including, but not limited to, non-volatile media, volatile media, and transmission media. Non-limiting examples of non-volatile media include optical disks, solid state drives, magnetic disks, and magneto-optical disks, for example hard disk 241 or removable media drive 242. Non-limiting examples of volatile media include dynamic memory, for example system memory 230. Non-limiting examples of transmission media include coaxial cables, copper wire, and fiber optics, including the wires that make up the bus 221. Transmission media may also take the form of acoustic or light waves, for example those generated during radio wave and infrared data communications.

The computing environment 200 may further include the computer system 210 operating in a networked environment using logical connections to local computing device 106 and one or more other devices, for example a personal computer (laptop or desktop), mobile devices (e.g., patient mobile devices), a server, a router, a network PC, a peer device or other common network node, and typically includes many or all of the elements described above relative to computer system 210. When used in a networking environment, computer system 210 may include modem 272 for establishing communications over a network 120, for example the Internet. Modem 272 may be connected to system bus 221 via network interface 270, or via another appropriate mechanism.

Network 120, as shown in FIGS. 2 and 3, may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 210 and other computers (e.g., local computing device 106).

Figure 4:
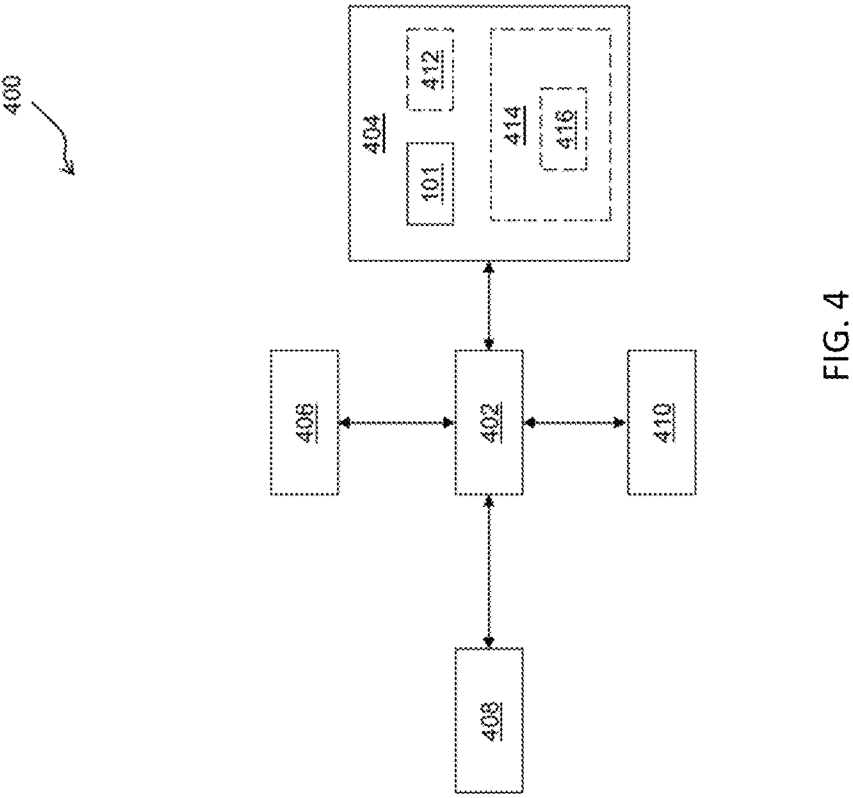
FIG. 4 is a block diagram of an example device in which one or more features of the disclosure can be implemented according to one or more embodiments.

FIG. 4 is a block diagram of an example device 400 in which one or more features of the disclosure can be implemented. The device 400 may be local computing device 106, for example. The device 400 can include, for example, a computer, a gaming device, a handheld device, a set-top box, a television, a mobile phone, or a tablet computer. The device 400 includes a processor 402, a memory 404, a storage device 406, one or more input devices 408, and one or more output devices 410. The device 400 can also optionally include an input driver 412 and an output driver 414. It is understood that the device 400 can include additional components not shown in FIG. 4 including an artificial intelligence accelerator.

In various alternatives, the processor 402 includes a central processing unit (CPU), a graphics processing unit (GPU), a CPU and GPU located on the same die, or one or more processor cores, wherein each processor core can be a CPU or a GPU. In various alternatives, the memory 404 is located on the same die as the processor 402, or is located separately from the processor 402. The memory 404 includes a volatile or non-volatile memory, for example, random access memory (RAM), dynamic RAM, or a cache. By way of example, the map revision techniques described herein are implemented as a processor executable code or software that can be stored on the memory 404 (as shown) and executed by processor 402, and rooted in process operations by, and in processing hardware of, the example device 400.

The storage device 406 includes a fixed or removable storage means, for example, a hard disk drive, a solid-state drive, an optical disk, or a flash drive. The input devices 408 include, without limitation, a keyboard, a keypad, a touch screen, a touch pad, a detector, a microphone, an accelerometer, a gyroscope, a biometric scanner, or a network connection (e.g., a wireless local area network card for transmission and/or reception of wireless IEEE 802 signals). The output devices 410 include, without limitation, a display device, a speaker, a printer, a haptic feedback device, one or more lights, an antenna, or a network connection (e.g., a wireless local area network card for transmission and/or reception of wireless IEEE 802 signals).

The input driver 412 communicates with the processor 402 and the input devices 408, and permits the processor 402 to receive input from the input devices 408. The output driver 414 communicates with the processor 402 and the output devices 410, and permits the processor 402 to send output to the output devices 410. It is noted that the input driver 412 and the output driver 414 are optional components, and that the device 400 will operate in the same manner if the input driver 412 and the output driver 414 are not present. The output driver 414 includes an accelerated processing device ("APD") 416 which communicates to a display device as represented by the output devices 410. The APD 416 accepts compute commands and graphics rendering commands from processor 402, processes those compute and graphics rendering commands, and provides pixel output to display device for display. As described in further detail below, the APD 416 includes one or more parallel processing units to perform computations in accordance with a single-instruction-multiple-data ("SIMD") paradigm. Thus, although various functionality is described herein as being performed by or in conjunction with the APD 416, in various alternatives, the functionality described as being performed by the APD 416 is additionally or alternatively performed by other computing devices having similar capabilities that are not driven by a host processor (e.g., processor 402) and provides graphical output to a display device. For example, it is contemplated that any processing system that performs processing tasks in accordance with a SIMD paradigm may perform the functionality described herein. Alternatively, it is contemplated that computing systems that do not perform processing tasks in accordance with a SIMD paradigm perform the functionality described herein.

Figures 5A, 5B:
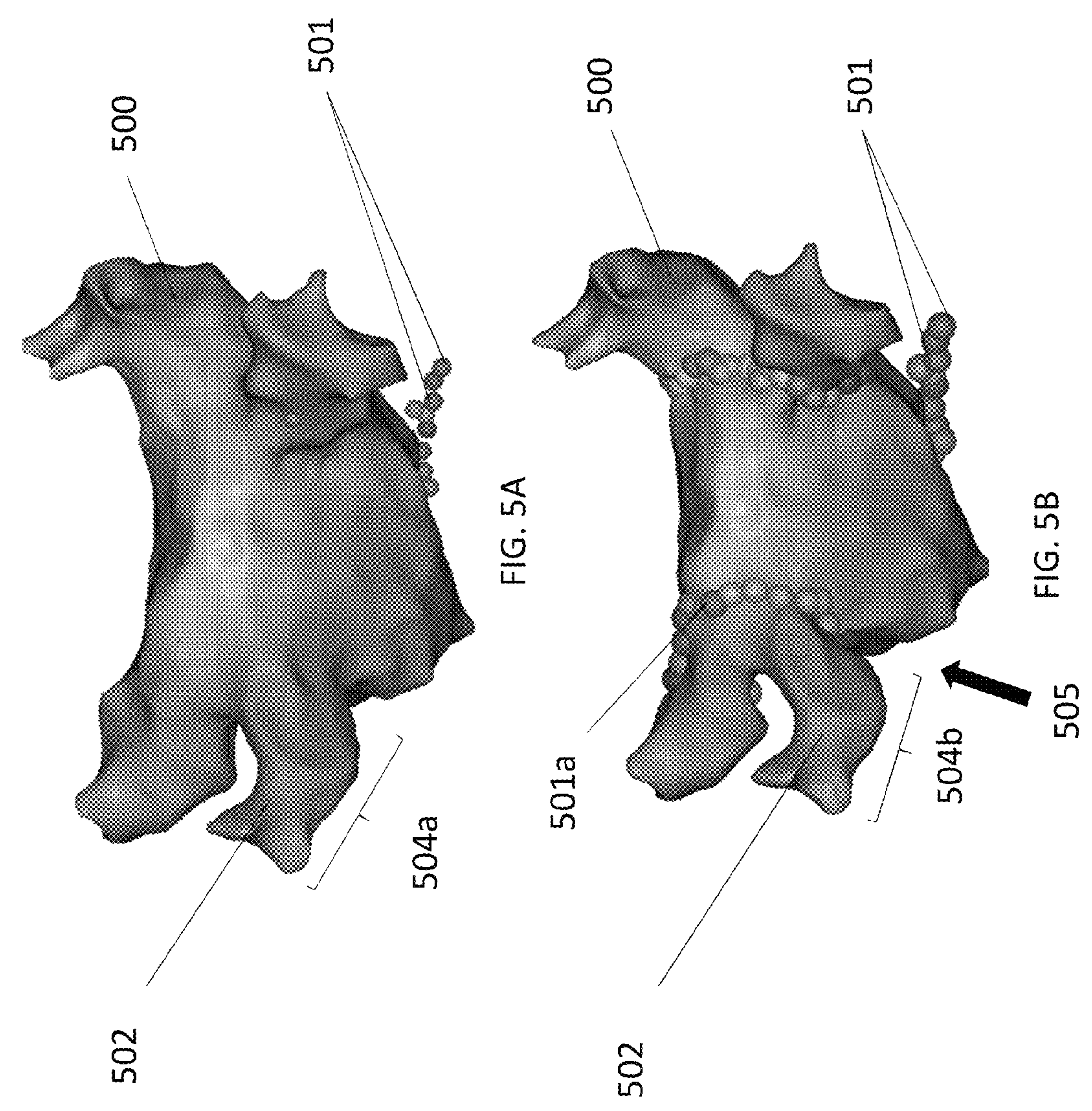
FIG. 5A depicts an electro-anatomical map of the heart prior to performing an anatomy fit for ablation tags, according to an example.
FIG. 5B depicts an electro-anatomical map of the heart after performance of an anatomy fit for ablation tags, according to an example.

FIG. 5A depicts an electro-anatomical map of heart 500 prior to performing an anatomy fit for ablation tags, according to an example. Heart 500 includes a pulmonary vein 502, which extends along a length 504*a*. Vein 502 has a substantially tubular shape along length 504*a*. In FIG. 5A, the substantially tubular shape of vein 502 has a cross-sectional size that exhibits a variation along length 504*a* consistent with a normal (healthy) vein. The electro-anatomical map also includes a plurality of tags 501. One example of a tag 501 is an ablation tag, which objectively identifies and annotates a site on the electro-anatomical map whenever predefined criteria such as catheter stability, time, contact force, or impedance drop are fulfilled. One example of an ablation tag is provided by The CARTO VISITAG™ system sold by Biosense Webster. In an embodiment of that system, the system calculates an index known as the Ablation Tag Index, which is a numerical value reflecting the quality and effectiveness of the ablation at a specific location. This index helps the electrophysiologist assess whether sufficient tissue has been treated to achieve the desired therapeutic effect. This system is often integrated with a 3D mapping system, which allows the electrophysiologist to visualize the cardiac anatomy in three dimensions. This integration helps guide the catheter to the targeted areas and provides a comprehensive view of the ablation procedure. In FIG. 5A, ablation tags 501 are shown on the map, and correspond to the locations of ablation sites.

In some examples, during a medical procedure such as a cardiac ablation, a fast anatomical map (FAM) (shown for example in FIGS. 5A and 5B) is generated and used for providing a 3D map of heart 500. The points used to generate the FAM are collected without regards to the respiration of the heart, or other conditions such as the pushing of the catheter against a tissue wall. The fact that such points are used to generate the FAM can result in the FAM being too large. In other examples, vein 502 may lack accuracy on the FAM due to a lack of data points. FIG. 5B depicts an electro-anatomical map of the heart with additional ablation tags 501*a*. Ablation tags 501*a* pass under vein 502 and continue around the surface of the heart.

In some examples, a technique is performed to conform or fit the FAM (which as mentioned above can be oversized or inaccurate) to the anatomy defined by ablation tags 501*a*. In some cases, this occurs when the physician is ablating, the catheter is in contact with the tissue, but the ablating electrodes are not visualized on the surface (as the surface is oversized). In response, a technician shaves the FAM to ensure that the ablation tag is placed on the surface and not inside the surface. This process requires "fitting" the anatomy in such a way that the ablation tags are placed correctly on the surface. During this fitting, the location information of the ablation tags 501, 501*a* is considered more accurate and is therefore weighted more heavily at the locations of the ablation tags than other data used to generate the FAM. In the example of FIG. 5B, the anatomy fit results in a visual artifact that causes the underside of vein 502 to appear pinched at the location identified by arrow 505, where vein 502 meets the heart chamber. This "pinching" artifact results when the anatomy fit causes the portions of the heart shown on the map proximate the ablation tags to shrink without shrinking or adjusting remaining portions of the FAM, and causes vein 502 to erroneously to take on an appearance consistent with stenosis. As explained below, the techniques described herein provide a solution for removing this artifact from the FAM by conforming the remainder of vein 502 (not proximate ablation tags 501*a*) in a manner consistent with the shrinkage of vein 502 proximate tags 501*a*, so that vein 502 no longer appears to suffer from stenosis. The techniques described herein are not limited to correction of artifacts resembling stenosis, but apply more generally to the processing of FAMs which include data points of varying levels of accuracy.

Figure 6:
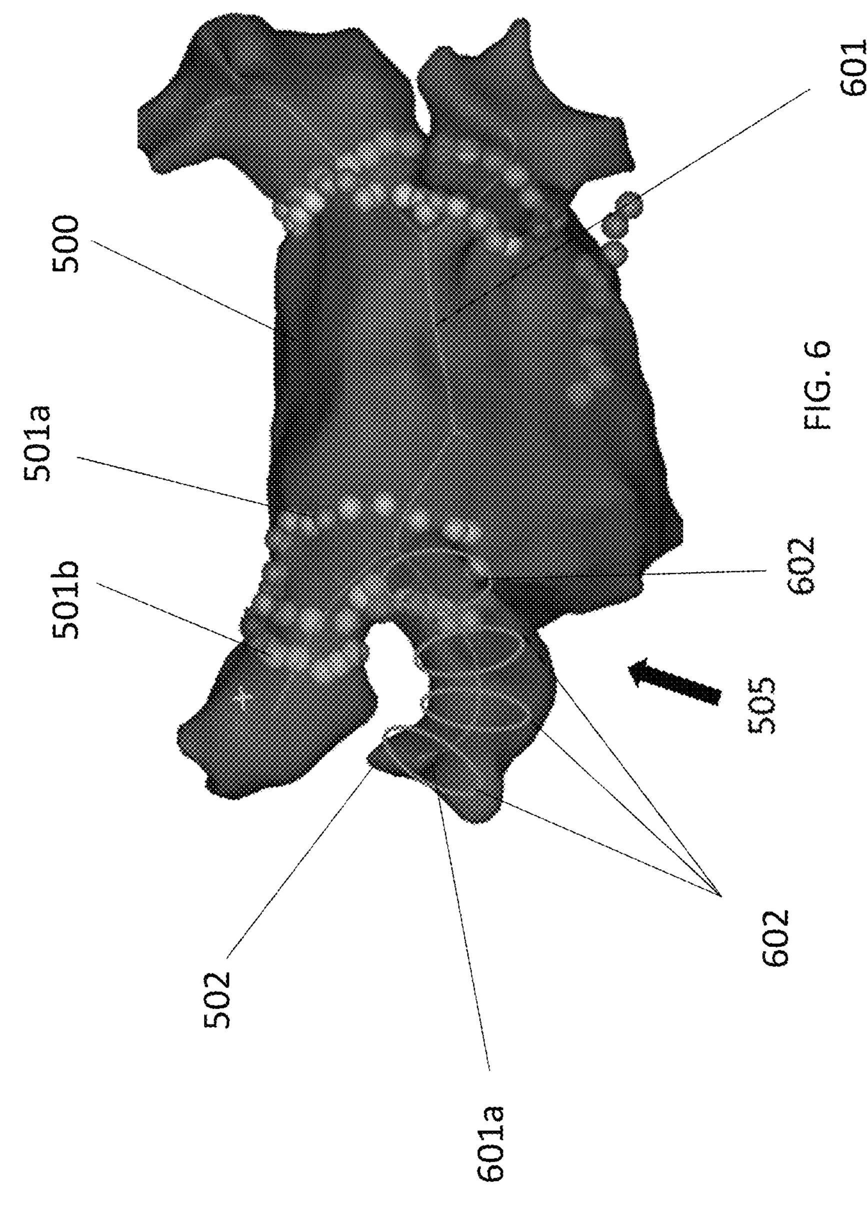
FIG. 6 depicts an electro-anatomical map of the heart along with its medial axis, according to an example.

FIG. 6 depicts an electro-anatomical map of the heart along with its medial axis, according to an example. In contrast to FIG. 5B where only ablation tags on the front surface of the heart were shown, in FIG. 6, ablation tags 501*a* on the front surface are shown using a solid dot, while ablation tags 501*b* on the back surface of the heart are shown with a dot in silhouette. A medial axis 601 of heart 500, together with a medial axis 601*a* of vein 502, are also shown. In some examples, system 100 determines and displays medial axes 601, 601*a* during an ablation procedure. A medial axis, sometimes referred to as the skeleton or centerline, is a geometric concept used in computational geometry and represents a set of points within a shape where there is more than one point equidistant to the boundary of the shape. The medial axis is often considered to represent the core or central part of a shape. In medical imaging, for example, the medial axis can be used to represent the central structure of an organ such as heart 500. While in the example of FIG. 6, the entirety of medial axis 601 is shown as being determined by system 100, in other examples (e.g., the example of FIG. 11) only one or more points on the medial axis are estimated. It will be understood that the references herein to "estimating" a point on the medial axis include both selection of a point on a previously calculated medial axis, as well as other techniques wherein one or more points along the medial axis are estimated.

Referring still to FIG. 6, as part of the technique for removing the "pinching" artifact identified with arrow 505 from the map, system 100 calculates at least one best-fitting ellipse 602, which passes through and lies in a plane perpendicular to medial axis 601*a* within vein 502. In some examples, best-fitting ellipse 602 is an ellipse that is determined to be the most appropriate or optimal representation of the set of data points represented by ablation tags on the surface of vein 502 in the plane of the ellipse. Fitting an ellipse to these points involves finding the ellipse that minimizes some measure of the difference between the ellipse and the data points on the surface of vein 502 in the plane of the ellipse. There are various methods for fitting an ellipse to a set of points, and the techniques described herein are not limited to a specific method for determining a best-fitting ellipse. A common approach for determining a best-fitting ellipse that is applicable to the techniques described herein is the least squares method, where the sum of the squared distances between the data points on the surface of vein 502 in the plane of the ellipse is minimized. It will be understood that a best-fitting circle is a specific case of an ellipse where the two foci coincide at the center, resulting in zero eccentricity. While the description set forth herein uses best-fitting ellipses for conforming the FAM (and, e.g., vein 502) to the size information provided by ablation tags 501*a*, use of other best-fitting shapes including best-fitting circles and best fitting closed-splines are within the scope of this disclosure. A best-fitting closed-spline refers to a spline curve that has been adjusted or fitted to a set of data points in such a way that it minimizes some measure of the difference between the spline and the given data.

In some examples, after a best-fitting ellipse is determined based on the collected data points, the size of the best-fitting ellipse is compared to minimum and/or maximum thresholds. In one example, these thresholds correspond to the minimum and maximum vein sizes associated with a typical vein size for a person having a profile similar to that of the patient. In these examples, if the best fitting ellipse is less than minimum threshold and/or greater than the maximum threshold, the best-fitting ellipse calculated based on the collected data points is not used for further calculations. In some such examples, an ellipse equal in size to the minimum threshold is substituted in the case where the best-fitting ellipse calculated from the collected data points is less than the minimum; and/or an ellipse equal in size to the maximum threshold is substituted in the case where the best-fitting ellipse calculated from the collected data points is more than the maximum.

In the embodiment of FIG. 6, data points corresponding to ablation tags are not available at locations other than the area proximate the right-most best-fitting ellipse 602. In such circumstances, system 100 may lack the data points required to separately calculate further best-fitting ellipses along the medial axis. Instead of calculating such further best-fitting ellipses, in the embodiment of FIG. 6 copies of the right-most ellipse are projected along the medial axis at an angle normal thereto, as shown.

Figure 7:
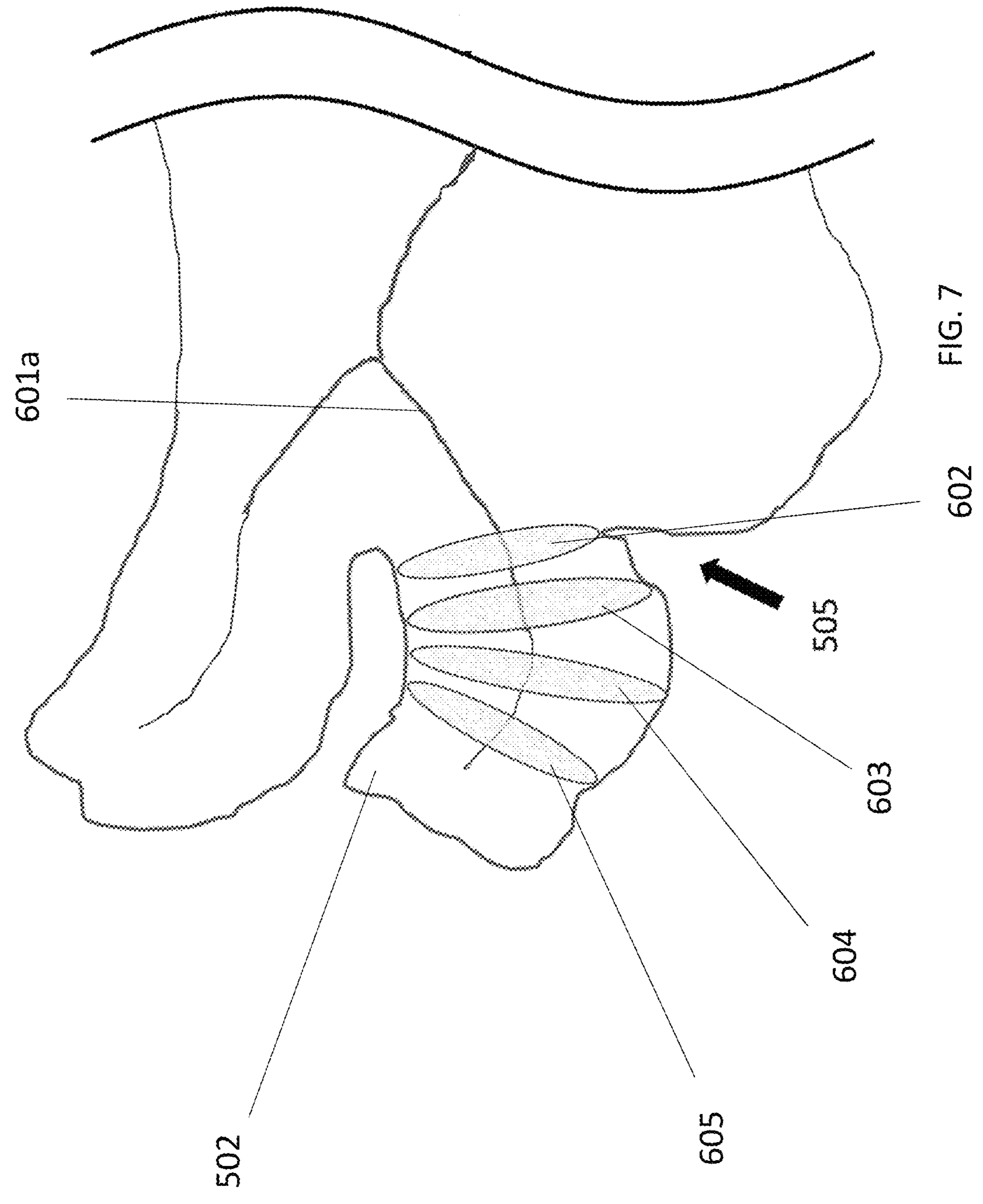
FIG. 7 depicts an electro-anatomical map of a pulmonary vein showing its medial axis and several best-filling ellipses positioned along the medial axis, according to an example.

FIG. 7 depicts an electro-anatomical map of pulmonary vein 502 showing its medial axis 601*a* according to an alternative embodiment where system 100 separately calculates additional best-fitting ellipses 603-605, each of which passes through and lies in a plane perpendicular to medial axis 601*a* within vein 502. In the example shown, best fitting ellipse 602*a* is located proximate the location of ablation tags 501*a*, 501*b* (not shown), which, as described above, correspond more closely to the actual size of the vein than other points on the FAM. Best-fitting ellipses 603-605 are calculated based on available data (e.g., further ablation tags corresponding to vein 502) positioned at different cross-sections of the mapped volume of vein 502 normal to the medial axis 601*a*. In one example, the length of the major axis and the length of the minor axis of each of best-fitting ellipses 603-605 is reduced so as to correspond or be equal to the length of the major axis and the length of the minor axis, respectively, of best-fitting ellipse 602. In another embodiment, information indicative of the size of the vein is derived from a pre-acquired image such as a CT or MRI and used for adjusting or shrinking ellipses 603-605. In a further embodiment, information of the size of the vein is estimated from the size of other veins (e.g., 2-3 other veins) depicted in the electro-anatomical map, and this estimate is used for adjusting or shrinking ellipses 602-605. In a still further embodiment, information indicative of the amount of shaving that will be required for a vein is estimated based on the amount of shaving required for other veins, and this estimate is used for adjusting or shrinking ellipses 602-605. While in the example shown, four best-fitting ellipses are used along the length of vein 502, any suitable number of best-fitting ellipses can be used for implementing the techniques described herein. After best-fitting ellipses 603-605 are each reduced to a size that more closely corresponds to that of best-fitting ellipse 602, a revised volume for vein 502 is determined by the mapping system, as explained more fully below.

Figure 8:
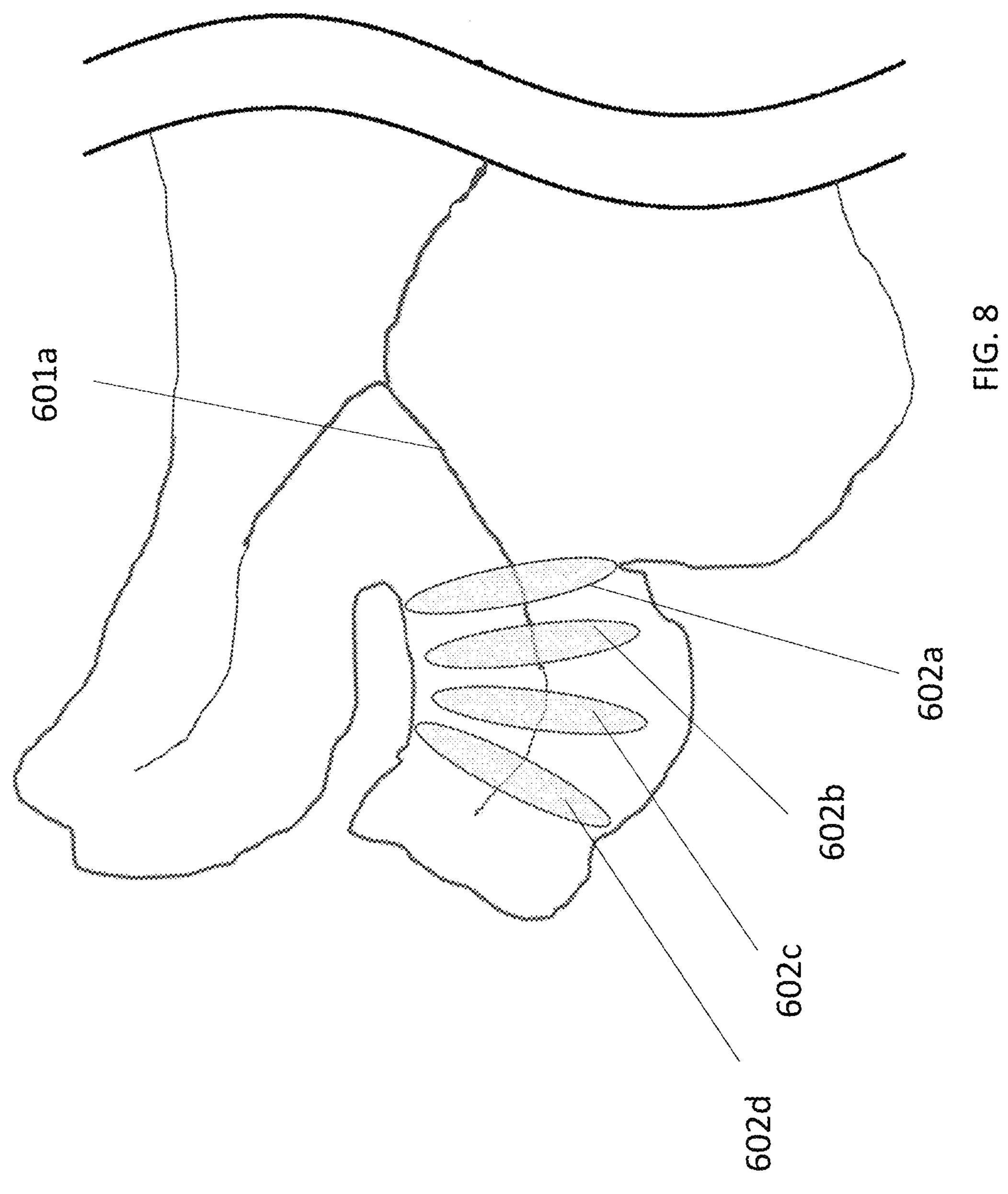
FIG. 8 depicts several ellipses for generating a tubular shape along the medial axis of the pulmonary vein of FIG. 7, according to an example.

FIG. 8 depicts an example of a technique for removing the “pinching” artifact similar to that of FIG. 6, except copies 602*b*-602*d* of the right-most best-fitting ellipse 602 are projected along the medial axis at an angle normal thereto. After copies 602*b*-*d* are projected along the medial axis, a revised volume for vein 502 is determined by the mapping system, as explained more fully below. While in the example shown, four copies of ellipse 602*a* are used along the length of vein 502, any suitable number of copies can be used for implementing the techniques described herein.

Figure 9:
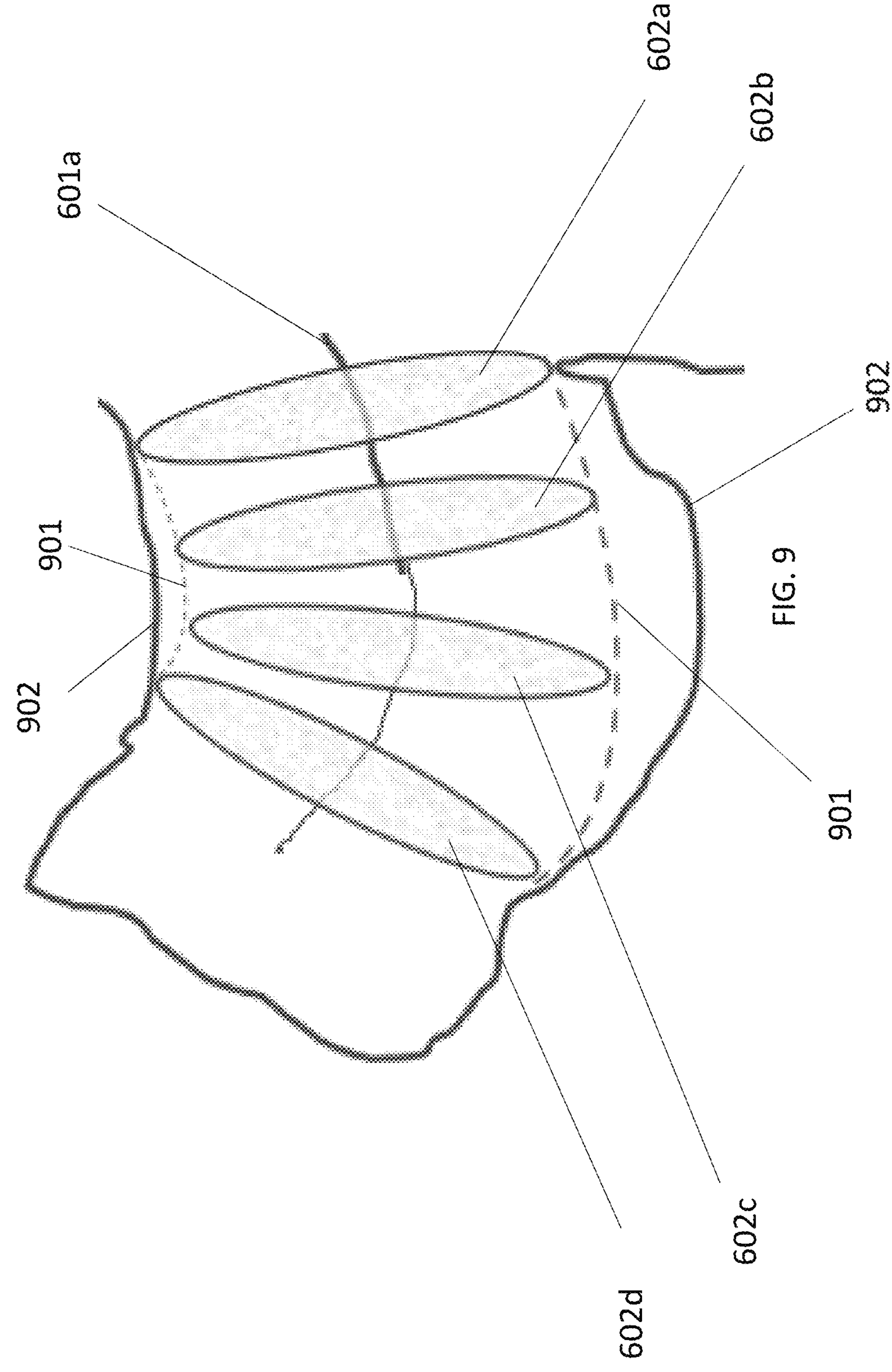
FIG. 9 depicts a tubular shape that is used for removing data points from the map, according to an example.

After calculation of the ellipses described in connection with the examples of FIGS. 6-8, a revised volume for vein 502 is determined by the mapping system. In the example of FIG. 9, system 100 calculates a new volume 901 (corresponding to a revised surface of vein 502) by interpolating between the boundaries of copies 602*a*-*d* of ellipse 601*a* along medial axis 601*a*. For purposes of the techniques described herein, volume 901 is considered to be a generalized cylinder or ruled surface that extends along medial axis 601*a* like a pipe or tube; however, because volume 901 corresponds to a vein, it will not correspond in shape to a perfect or regular cylinder. Following calculation of volume 901, the voxels in the FAM between original volume 902 and new volume 901 are removed, and an updated version of vein 502 (without the artifact described above) is displayed. While in the example described above, the voxels between original volume 902 and new volume 901 are removed in an automated manner in a single step (e.g., actuated by a single-click of an operator via a user interface), it will be understood that removal of these voxels can be performed in multiple steps using an automated shaving procedure where voxels from volume 902 are shaved in layers until new volume 901 is reached. In some examples, this step-wise procedure is accomplished by an operator shaving successive layers from original volume 902 via a user interface on display 27.

While in the example of FIG. 9, the volume 901 is calculated based on four copies of one best-fitting ellipse, it will be understood that in other examples such as that shown in FIG. 7, additional separately calculated best-fitting ellipses are used for the calculation of volume 901. In some examples, two or more best fitting ellipses are used. In some examples, the number of best-fitting ellipses used for calculating tubular volume 901 involves a compromise between accuracy and efficiency. In these examples, the computational time required to compute each best-fitting ellipse is balanced against the increased accuracy of volume 901 associated with each additional best-fitting ellipse, and an optimum number of best-fitting ellipses is chosen based on these considerations.

Figure 10:
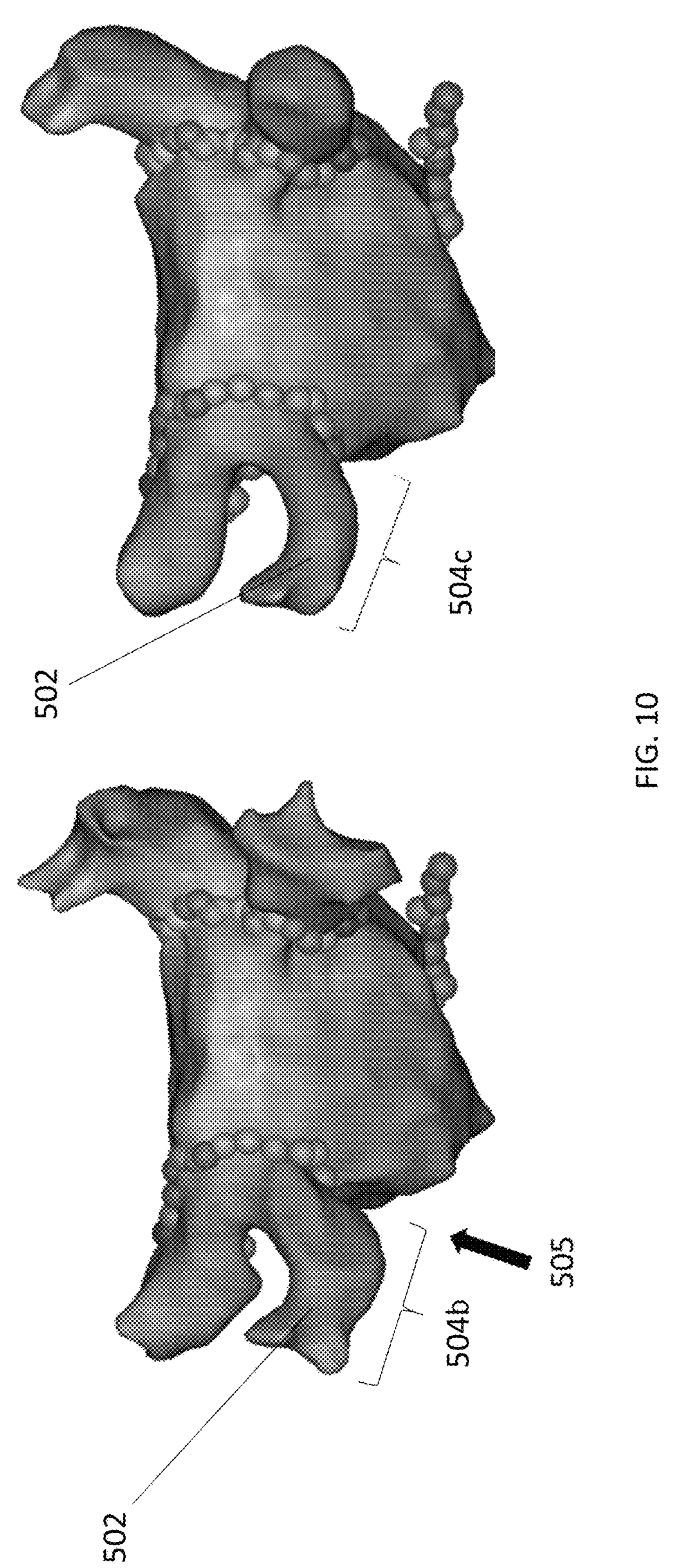
FIG. 10 depicts a side-by-side comparison of the map of FIG. 5B and an updated version of that map which has been revised in accordance with the techniques described herein, according to an example.

FIG. 10 depicts a side-by-side comparison of the map of FIG. 5B (left) and an updated version of that map (right) which has been revised in accordance with the techniques described herein, according to an example. In the example of FIG. 5B, the anatomy fit resulted in a visual artifact that caused vein 502 to appear pinched at the location identified by arrow 505, where vein 502 meets the heart chamber. The map shown on the right in FIG. 10 has been revised in accordance with the techniques described above such that the remaining portions of vein 502 along length 504*c* have been shrunk to more closely correspond in size to the portion of the vein proximate area 505. In the revised map, vein 502 appears as healthy, and no longer resembles one suffering from stenosis.

While, in the above example, the techniques for revising the FAM are described in connection with vein 502, the techniques described herein are not limited to veins, and can be applied to other anatomical structures in the heart or elsewhere in the human body.

Figure 11:
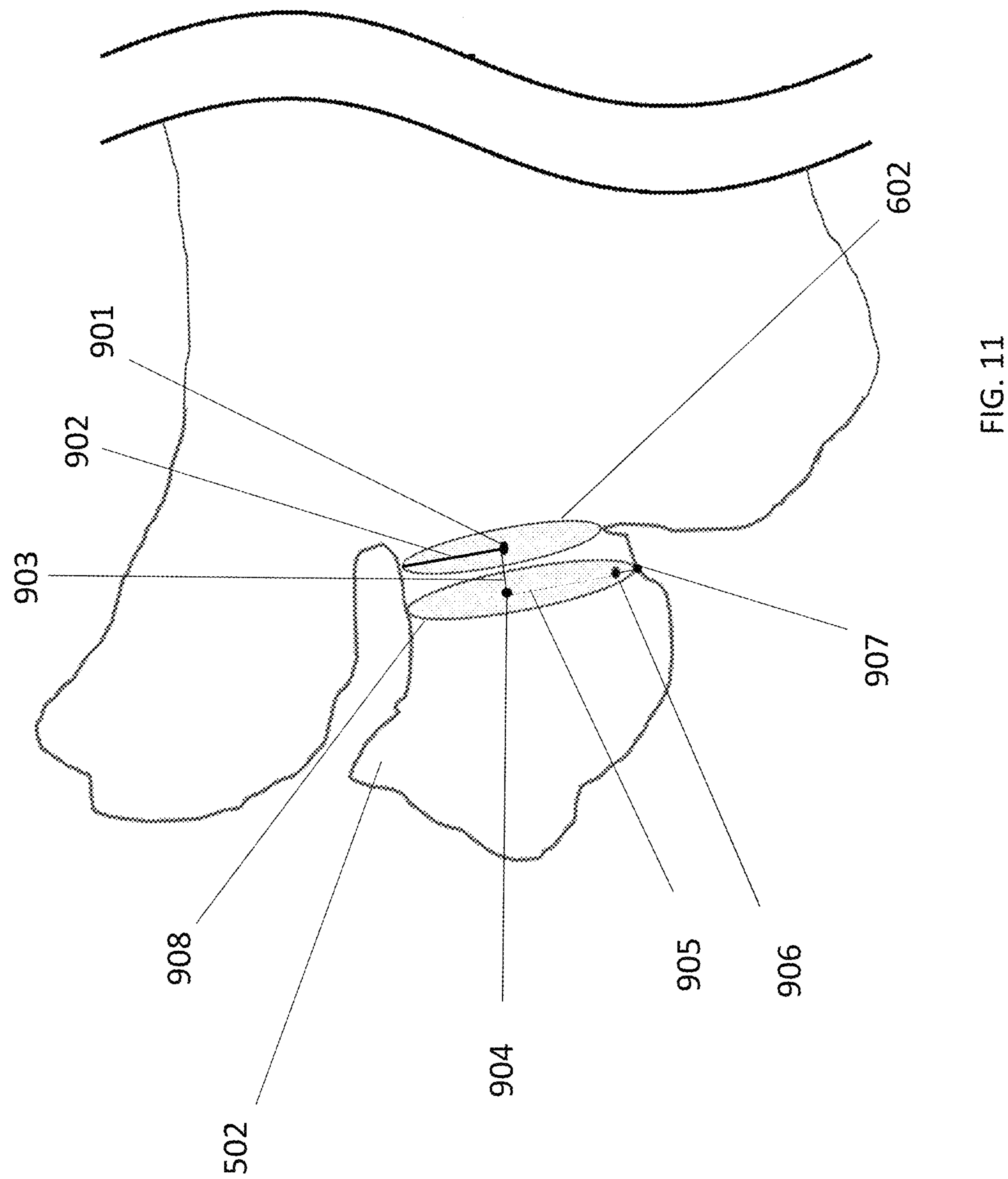
FIG. 11 depicts an electro-anatomical map of the heart, according to a further example.

FIG. 11 depicts an electro-anatomical map of the heart, according to a further example. While in the examples of FIGS. 6-8, sufficient data points to define all or most of medial axis 601*a* were calculated, in the example of FIG. 11 the medial axis as a whole is not calculated. Rather, in the example of FIG. 11, a limited number of data points (e.g., one or more data points) are estimated as being along the medial axis. In the example of FIG. 11, best-fitting ellipse 602 is calculated to be the most appropriate or optimal representation of the set of data points represented by ablation tags on the surface of vein 502 in the plane of the ellipse, as described above. System 100 calculates a center point 901 of ellipse 602, and a radius 902 of ellipse 602. In one embodiment, system 100 estimates that center point 901 lies along the medial axis (not shown) of vein 502. System 100 projects a distance corresponding to line 903 in a direction normal the plane of ellipse 602 to estimate a further data point 904 along the medial axis. System 100 identifies point 906 by projecting from point 904 along line 905 a distance corresponding to the length of radius 902. Line 905 is normal to line 903. System 100 identifies a point 907 on the map surface closest to point 906, and uses point 907 to calculate closed curve 908 which estimates the surface of vein 502 at a cross-section passing through point 904. Techniques for calculating closed curve 908 are disclosed in connection with the discussion of, e.g., FIG. 3 of U.S. Pat. No. 11,461,895, owned by the assignee of the present application. The contents of U.S. Pat. No. 11,461,895 is incorporated by reference in its entirety. While in FIG. 11, only a single closed curve is shown, it will be understood that in other examples system 100 calculates multiple additional closed curves along vein 502 by repeating the process described above, until multiple closed curves are determined along the length of the vein.

Continuing with the example of FIG. 11, system 100 calculates a new volume (corresponding to a revised surface of vein 502) by interpolating between the boundaries of ellipse 602 and each successive closed curve calculated long vein 502. This process is similar to that described in connection with FIG. 9, except that closed curves are substituted for one or more of the ellipses shown in FIG. 9. The new volume corresponds to a generalized cylinder or ruled surface that extends along the vein like a pipe or tube. Following calculation of the new volume, the voxels in the FAM between original volume and new volume are removed, and an updated version of vein 502 is displayed. The voxels between original volume and the new volume 901 are removed either in an automated manner in a single step (e.g., actuated by a single-click of an operator via a user interface), or in multiple steps using an automated shaving procedure where voxels from volume the old volume are shaved in layers until new volume is reached. In some examples, this step-wise procedure is accomplished by an operator shaving successive layers from original volume via a user interface on display 27.

Figure 12:
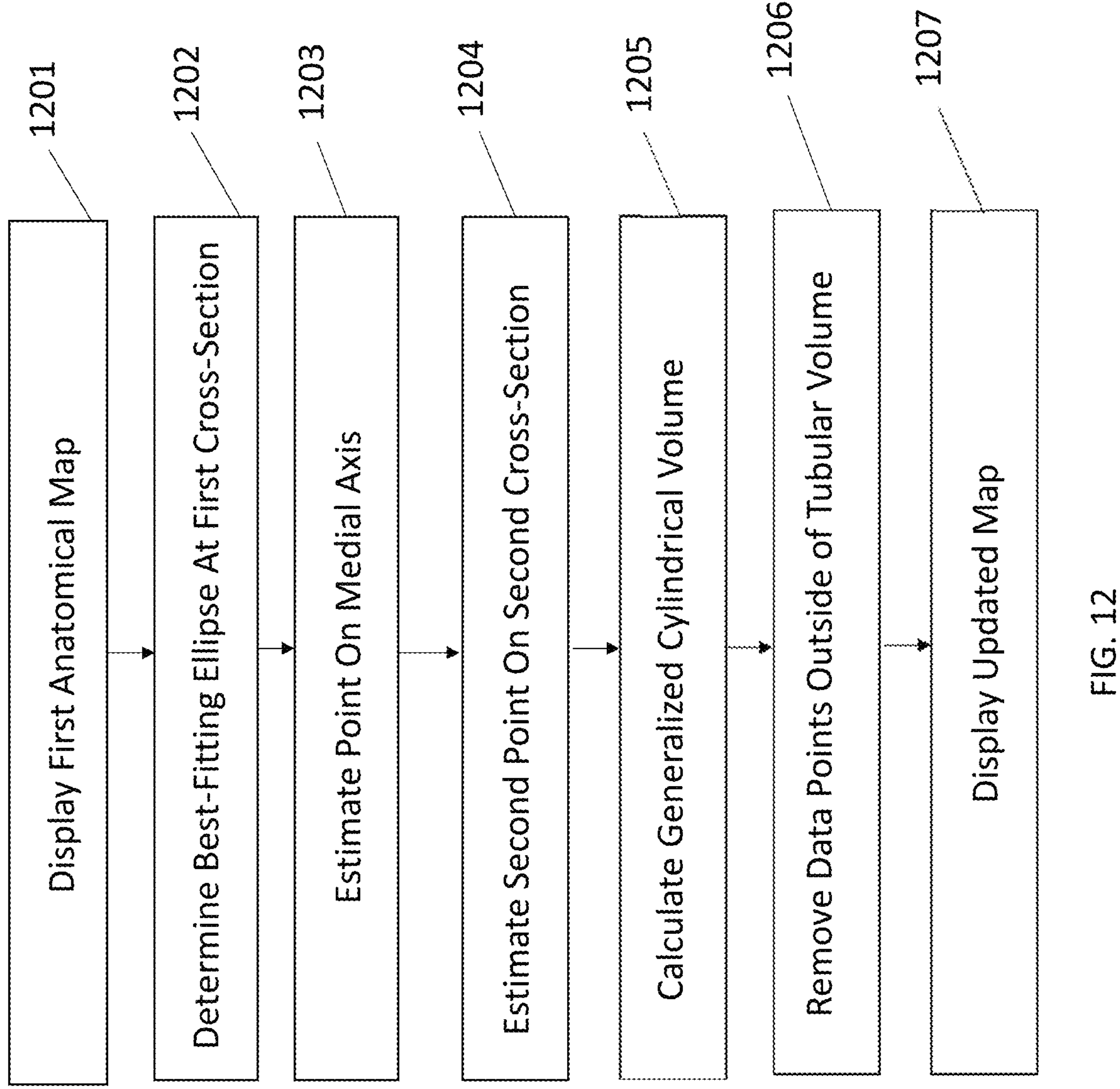
FIG. 12 depicts a method according to one or more embodiments.

Turning now to FIG. 12, a method 1200 is illustrated according to one or more exemplary embodiments. The method 1200 is an example set of operations rooted in and executed by the workstation 55 of FIG. 1, the local computing device 106 of FIG. 2, the remote computing system 108 of FIG. 2, and/or the example device 400 of FIG. 4. The method 1200 shows an example of how system 100 generates and presents maps of an anatomical structure (e.g., one or more 3D models) on a user interface, and revises such maps in accordance with the techniques set forth herein, for example during an EP procedure (e.g., an ablation procedure).

The method 1200 begins at block 1201, where a first electro-anatomical map that includes an anatomical structure having a mapped volume with a substantially tubular shape is displayed on a user interface. In one example, the first electro-anatomical map corresponds to the map shown in FIG. 5B, the anatomical structure having a mapped volume with a substantially tubular shape corresponds to vein 502 shown in FIG. 5B, and the user interface corresponds to a user interface displayed on display device 27 (shown in FIG. 1). In this example, the anatomical map depicts a 3D rendering of a heart, and includes features such as one or more ablation tags.

At block 1202, at a first cross-section of the mapped volume, a first best-fitting ellipse (or other best-fitting shape) is determined based on data points associated with the first cross-section of the mapped volume. In one example, the first best-fitting ellipse corresponds to ellipse 602 (in FIG. 7).

At block 1203, at least one point along a medial axis (e.g., axis 601*a*) of the mapped volume (e.g., vein 502) is estimated. While in the example of FIG. 6, the entirety of medial axis 601 is shown as being determined (or estimated) by system 100, in other examples (e.g., the example of FIG. 11) only one or more points on the medial axis are estimated. It will be understood that the references herein to “estimating” point(s) on the medial axis include both selection of a point on a previously calculated (estimated) medial axis, as well as other techniques (e.g., the techniques of FIG. 11) wherein one or more points along the medial axis are estimated.

In block 1204, at a second cross-section of the mapped volume, a second point along the medial axis on the second cross-section is estimated. In some examples, a copy of the first best-fitting ellipse is positioned at the second cross-section. In some such examples, further copies of the first best-fitting ellipse are positioned at further cross-sections along the vein in a direction normal to the estimated medial axis. In other examples, a second best-fitting ellipse is separately calculated and positioned at the second cross-section. In one example, the second best-fitting ellipse is initially calculated based on the original volume 902 of vein 502 and then revised (or, e.g., shrunk) to more closely correspond in size to the first best-fitting ellipse. In some such examples, further best-fitting ellipses (separately calculated) are positioned at further cross-sections along the vein in a direction normal to the estimated medial axis. In other embodiments, a combination of copies of the first-best fitting ellipse and other separately calculated best-fitting ellipses are position along the vein. As mentioned above, other best-fitting shapes are within the scope of the techniques described herein.

In block 1205, a generalized cylindrical volume is calculated along the estimated medial axis and spanning between the first cross-section and the second cross-section in accordance with the first best-fitting ellipse. In one example, the generalized cylindrical volume corresponds to volume 901 (in FIG. 9) and is determined by interpolating between the boundaries of the copies of the first best-betting ellipses, or between first and second best-fitting ellipses along the estimated medial axis. In some embodiments, where a plurality of best-fitting ellipses are determined along the length of vein 502, the volume is determined in block 1205 by interpolating between the boundaries of multiple best-fitting ellipses along the estimated medial axis. In block 1206, data points (or in some cases, voxels) that are outside of the volume are removed. In some examples, this step includes removing all voxels between new volume 901 and original volume 902, as shown in FIG. 9, and is performed in a single step or multiple steps by an operator during a medical procedure. In block 1207, a second electro-anatomical map (e.g., the map shown on the right side of FIG. 10) having an updated version of the anatomical structure generated without the removed data points is displayed on the user interface.

In some examples, the techniques in FIG. 12 are applied to a vein associated with a heart muscle and the data points associated with the first cross-section of the mapped volume correspond to ablation tags. In some such examples, at one or more of a plurality of additional cross-sections of the mapped volume normal to and along a length of the medial axis, the data points associated with the cross-section do not correspond to ablation tags. In some examples, the first best-fitting ellipse is a circle, and the substantially tubular shape is a substantially cylindrical shape. In some embodiments, the electro-anatomical map is a fast anatomical map that is generated during a cardiac ablation procedure.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. A computer readable medium, as used herein, is not to be construed as being transitory signals per se, for example radio waves or other freely propagating electromagnetic waves, electromagnetic waves propagating through a waveguide or other transmission media (e.g., light pulses passing through a fiber-optic cable), or electrical signals transmitted through a wire.

Examples of computer-readable media include electrical signals (transmitted over wired or wireless connections) and computer-readable storage media. Examples of computer-readable storage media include, but are not limited to, a register, cache memory, semiconductor memory devices, magnetic media (e.g., internal hard disks and removable disks), magneto-optical media, optical media (e.g., compact disks (CD) and digital versatile disks (DVDs)), a random access memory (RAM), a read-only memory (ROM), an erasable programmable read-only memory (EPROM or Flash memory), a static random access memory (SRAM), and a memory stick. A processor in association with software may be used to implement a radio frequency transceiver for use in a terminal, base station, or any host computer.

The terminology used herein is for the purpose of describing particular embodiments only and is not intended to be limiting. As used herein, the singular forms “a”, “an” and “the” are intended to include the plural forms as well, unless the context clearly indicates otherwise. It will be further understood that the terms “comprises” and/or “comprising,” when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A method for improving accuracy of an electro-anatomical map by automatically shaving a vein to reduce tubular-structure mapping artifacts, the method comprising:

displaying, on a screen, a first electro-anatomical map of a portion of a patient anatomy, the first electro-anatomical map comprising a mapped volume of an anatomical structure that is substantially tubular;

at a first cross-section of the mapped volume, determining a first best-fitting ellipse based on data points associated with the first cross-section of the mapped volume, wherein the first best-fitting ellipse is non-circular such that a major axis length of the first best-fitting ellipse is different from a minor axis length of the first best-fitting ellipse;

estimating a first point along a medial axis of the mapped volume based on a center of the first best-fitting ellipse;

estimating a second point along the medial axis of the mapped volume at a second cross-section of the mapped volume;

computing a generalized cylindrical volume spanning between at least the first cross-section and the second cross-section based on the medial axis;

removing, from a point cloud of mapped data points representing the mapped volume, mapped data points that are located outside the generalized cylindrical volume, wherein removing is performed without computing an intersection line between polygonal meshes of different anatomical structures; and displaying, on the screen, a revised electro-anatomical map based on the point cloud after removal of the mapped data points located outside the generalized cylindrical volume.

2. The method of claim 1, wherein estimating the second point comprises determining a plurality of medial-axis points along the medial axis, wherein the first cross-section and the second cross-section are each normal to the medial axis, and wherein the second point is selected from the plurality of medial-axis points.

3. The method of claim 1, wherein the anatomical structure comprises a vein associated with a heart muscle.

4. The method of claim 1, wherein the data points associated with the first cross-section correspond to ablation tags.

5. The method of claim 1, further comprising:

estimating one or more additional points along the medial axis at one or more additional cross-sections of the mapped volume, and computing the generalized cylindrical volume further based on the one or more additional points such that the generalized cylindrical volume spans the first cross-section, the second cross-section, and the one or more additional cross-sections.

6. The method of claim 4, wherein data points associated with at least one other cross-section of the mapped volume do not correspond to ablation tags.

7. The method of claim 1, wherein the generalized cylindrical volume is substantially cylindrical.

8. The method of claim 1, wherein the first electro-anatomical map comprises a fast anatomical map.

9. A system for improving accuracy of an electro-anatomical map by automatically shaving a vein to reduce tubular-structure mapping artifacts, the system comprising:

a memory configured to store map data comprising a point cloud of mapped data points representing a mapped volume of an anatomical structure that is substantially tubular; and a processor configured to:

cause display, on a screen, of a first electro-anatomical map of a portion of a patient anatomy, the first electro-anatomical map comprising the mapped volume;

at a first cross-section of the mapped volume, determine a first best-fitting ellipse based on data points associated with the first cross-section of the mapped volume, wherein the first best-fitting ellipse is non-circular such that a major axis length of the first best-fitting ellipse is different from a minor axis length of the first best-fitting ellipse;

estimate a first point along a medial axis of the mapped volume based on a center of the first best-fitting ellipse;

estimate a second point along the medial axis of the mapped volume at a second cross-section of the mapped volume;

compute a generalized cylindrical volume spanning between at least the first cross-section and the second cross-section based on the medial axis;

remove, from the point cloud of mapped data points, mapped data points that are located outside the generalized cylindrical volume, wherein removing is performed without computing an intersection line between polygonal meshes of different anatomical structures; and cause display, on the screen, of a revised electro-anatomical map based on the point cloud after removal of the mapped data points located outside the generalized cylindrical volume.

10. The system of claim 9, wherein the processor is configured to estimate the second point by determining a plurality of medial-axis points along the medial axis, wherein the first cross-section and the second cross-section are each normal to the medial axis, and wherein the second point is selected from the plurality of medial-axis points.

11. The system of claim 9, wherein the anatomical structure comprises a vein associated with a heart muscle.

12. The system of claim 9, wherein the processor is configured to determine that the data points associated with the first cross-section correspond to ablation tags.

13. The system of claim 9, wherein the processor is further configured to:

estimate one or more additional points along the medial axis at one or more additional cross-sections of the mapped volume, and compute the generalized cylindrical volume further based on the one or more additional points such that the generalized cylindrical volume spans the first cross-section, the second cross-section, and the one or more additional cross-sections.

14. The system of claim 12, wherein the processor is configured to determine that data points associated with at least one other cross-section of the mapped volume do not correspond to ablation tags.

15. The system of claim 9, wherein the generalized cylindrical volume is substantially cylindrical.

16. The system of claim 9, wherein the first electro-anatomical map comprises a fast anatomical map.

17. A non-transitory computer-readable medium for improving accuracy of an electro-anatomical map by automatically shaving a vein to reduce tubular-structure mapping artifacts, the non-transitory computer-readable medium having instructions stored thereon that, when executed by a processor, cause the processor to perform a method comprising:

displaying, on a screen, a first electro anatomical map of a portion of a patient anatomy, the first electro-anatomical map comprising a mapped volume of an anatomical structure that is substantially tubular;

at a first cross-section of the mapped volume, determining a first best-fitting ellipse based on data points associated with the first cross-section of the mapped volume, wherein the first best-fitting ellipse is non-circular such that a major axis length of the first best-fitting ellipse is different from a minor axis length of the first best-fitting ellipse;

estimating a first point along a medial axis of the mapped volume based on a center of the first best-fitting ellipse;

estimating a second point along the medial axis of the mapped volume at a second cross-section of the mapped volume;

computing a generalized cylindrical volume spanning between at least the first cross-section and the second cross-section based on the medial axis;

removing, from a point cloud of mapped data points representing the mapped volume, mapped data points that are located outside the generalized cylindrical volume, wherein removing is performed without computing an intersection line between polygonal meshes of different anatomical structures; and displaying, on the screen, a revised electro-anatomical map based on the point cloud after removal of the mapped data points located outside the generalized cylindrical volume.

18. The non-transitory computer-readable medium of claim 17, wherein estimating the second point comprises determining a plurality of medial-axis points along the medial axis, wherein the first cross-section and the second cross-section are each normal to the medial axis, and wherein the second point is selected from the plurality of medial-axis points.

19. The non-transitory computer-readable medium of claim 17, wherein the anatomical structure comprises a vein associated with a heart muscle.

20. The non-transitory computer-readable medium of claim 17, wherein the data points associated with the first cross-section correspond to ablation tags.

* * * * *